United States Patent [19]

Genn

[11] Plant 4,132

[45] Oct. 25, 1977

[54] WALNUT TREE

[75] Inventor: Olan R. Genn, Modesto, Calif.

[73] Assignees: Olan R. Genn; Fern F. Genn, both of Modesto, Calif.

[21] Appl. No.: 757,053

[22] Filed: Jan. 4, 1977

[51] Int. Cl.[2] ..... A01H 5/03

[52] U.S. Cl. ..... Plt./32

[58] Field of Search ..... Plt./32

*Primary Examiner*—Robert E. Bagwill

*Attorney, Agent, or Firm*—Roger B. Webster

[57] ABSTRACT

A cold-resistant, English walnut tree which is of medium size, vigorous, spreading, densely foliated with large, early season, elliptic leaves, very early and abundant in flowering, and a regular, very early bearer, with medium productivity, of small, round, uniform, thin and soft-shelled, well-sealed, well-fitted nuts having relatively large, plump kernels, the nuts—which drop off early—having hulls which often split so that the nuts drop free.

1 Drawing Figure

ORIGIN OF THE VARIETY

The herein claimed variety of walnut tree was purchased—assertedly as a seedling of the Carpathian walnut (unpatented)—from a commercial nursery and planted in the yard of a residence I occupied in Twin Falls, Idaho; such tree, in maturity, having evidenced certain characteristics which were recognized by me (as a County Agricultural Extension Agent) as being novel and distinct.

ASEXUAL REPRODUCTION OF THE VARIETY

Upon my recognition that the variety was novel and distinct, it was asexually reproduced by grafting onto Northern California black walnut (unpatented) rootstock; such reproduction having been undertaken, on my behalf, by a commercial nursery. In maturity, trees of the variety so reproduced ran true to the original tree in all respects.

SUMMARY OF THE VARIETY

The herein claimed variety of walnut tree is of medium size, vigorous, spreading, densely foliated with large, early season, elliptic leaves, very early and abundant in flowering, and a regular, very early bearer, with medium productivity, of small, round, uniform, thin and soft-shelled, well-sealed, well-filled nuts having relatively large, plump kernels, the nuts—which drop off early—having hulls which often split so that the nuts drop free; the tree being especially characterized by its resistance to extreme cold without serious damage. The tree has withstood cold weather in the range of 20°-25° below zero, with only minimal terminal growth freezeback, and which growth promptly reconstituted itself.

The present variety of walnut tree, while not particularly adapted to commercial growing—because of the small size of the nuts—is characterized in vigor, growth, and density such as to provide an excellent specimen shade tree or ornamental, with the further advantage of nuts which are quite desirable for domestic use; the kernels of the nuts being of excellent flavor. The nuts of the present variety generally resemble those of the Adams walnut tree (unpatented).

The present variety of walnut tree is additionally characterized—when in full maturity—by trunk bark which is white; i.e., substantially a whitewash color. Further, the branches of the tree—in natural growth—tend to extend from the trunk of the tree almost at a right angle, except the upper branches which turn upward toward the light.

BRIEF DESCRIPTION OF THE DRAWING

The drawing is an illustration, by photographic reproduction in color, of leaves and nuts on a twig, and separate nuts.

DESCRIPTION OF THE VARIETY

The botanical details of this new and distinct variety of walnut tree—with color definitions (except those in common color terms) referenced to Maerz and Paul Dictionary of Color—are as follows:

Tree
- *Size (at maturity).*—Medium.
- *Vigor.*—Vigorous.

Trunk:
- *Form.*—Medium.
- *Texture.*—Smooth.
- *Color of Bark.*—White when mature.

Branches:
- *Form.*—Stocky.
- *Texture.*—Smooth.
- *Lenticels.*—Few. Small.
- *Branching Habit.*—Spreading.
- *Color.*—New Wood: Green — very glossy. Mature Wood: Brown — very glossy.

Foliage:
- *Quantity.*—Abundant.
- *Density.*—Dense.

Leaves:
- *Compound leaves.*—Size: Large. Average length — 9"-13". Time of leafing: Early.
- *Leaflets.*—Size: Large. Average length — 8". Average width — 1¾". Shape: Elliptic. Thickness: Medium. Texture: Rugose. Margin: Glandular. Petiole: Long. Slender. Glands: Wanting. Stipules: Wanting. Color: Top side — Medium green (23-J-7). Under side — Lighter green (22-K-5).

Flowering habit:
- *Age at which tree starts producing catkins.*—Very early.
- *Number of catkins produced.*—Average.
- *Size of catkins.*—Very large.
- *Time of pollen shedding.*—Early.
- *Age at which tree starts producing pistillate flowers.*-

—Very early.

*Number of pistillate flowers produced by young trees.*—Abundant.

*Number of pistillate flowers produced by mature trees.*—Abundant.

*Percentage of lateral buds on long shoots(about 3 feet) of previous season's growth which produce pistillate flowers.*—80%.

*Number of pistillate flowers per inflorescence.*—Average — 2 (3-20%).

*Time when pistillate flowers are receptive.*—Very early.

*Coincidence of staminate and pistillate bloom.*—Good.

Crop:

*Bearing.*—Regular bearer.

*Productivity.*—Medium. Very late hard freeze reduces yield, but without substantial damage to the tree.

*Ripening period.*—Aug. 25th–Sept. 15th. Very early, as compared to the Adams walnut.

*Evenness of maturity (period between time first and last nuts are ready to harvest).*—Very short.

*Quality.*—Best.

*Distribution of nuts on tree.*—In pairs on 80% of terminals. Nuts appear on every short branch and along long year-old shoots where there is seemingly only a bud when new growth starts.

*Tenacity.*—Tendency to drop off early. Easy to harvest. Easy to hull. Very frequently the hull cracks and nuts fall free, and—unless harvested—the tree drops all nuts over a 20 day period. Hulls remain fleshy and thick until nuts drop out.

Hull:

*Outer surface.*—Smooth.

*Form.*—Regular.

*Thickness.*—Thick.

*Flesh.*—Fleshy.

*Suture.*—Ridged along sides. Smooth over ends.

*Dehiscence.*—Opens freely.

*Splitting.*—No pattern. Many cracks in all directions.

*Color.*—Light green (22-L-6). Spotted with very small yellow speckles. Hulls remain green until frost.

Nut:

*Size.*—Small. Average length — $1\frac{1}{4}''$. Average diameter in suture plane — $1\frac{3}{8}''$. Average diameter check to cheek — $1\frac{3}{8}''$.

*Uniformity of size.*—Little variation.

*Form.*—Rounded.

*Blossom end.*—Rounded.

*Basal end.*—Rounded.

*Weight.*—Weight of ten nuts — 107 grams. Weight of ten kernels — 47 grams. Average percentage kernel to nut — 44.8%.

*Thickness of shell.*—Medium.

*Hardness of shell.*—Soft.

*Seal of shell.*—Very good.

*Roughness of shell.*—Medium.

*Fill.*—Very good.

*Color.*—Light brown (13-K-7).

Kernel:

*Size.*—Large relative to nut size.

*Plumpness.*—Very plump.

*Shrivel.*—None.

*Speckling.*—None.

*Veining.*—None to lightly.

*Flavor.*—Excellent.

*Color.*—Beige (11-I-4).

Resistance to disease: Good.

Resistance to insects: Good.

The walnut tree and its nuts herein described may vary in slight detail due to climatic and soil conditions under which the variety may be grown; the present description being of the variety as grown in Twin Falls, Idaho.

I claim:

1. A new and distinct variety of English walnut tree, substantially as illustrated and described, which is of medium size, vigorous, spreading densely foliated with large, early season, elliptic leaves, very early and abundant in flowering, and a regular, very early bearer, with medium productivity, of small, round, uniform, thin and soft-shelled, well-sealed, well-filled nuts having relatively large, plump kernels, the nuts—which drop off early—having hulls which often split so that the nuts drop free; the tree being especially characterized by its resistance to extreme cold without serious damage.

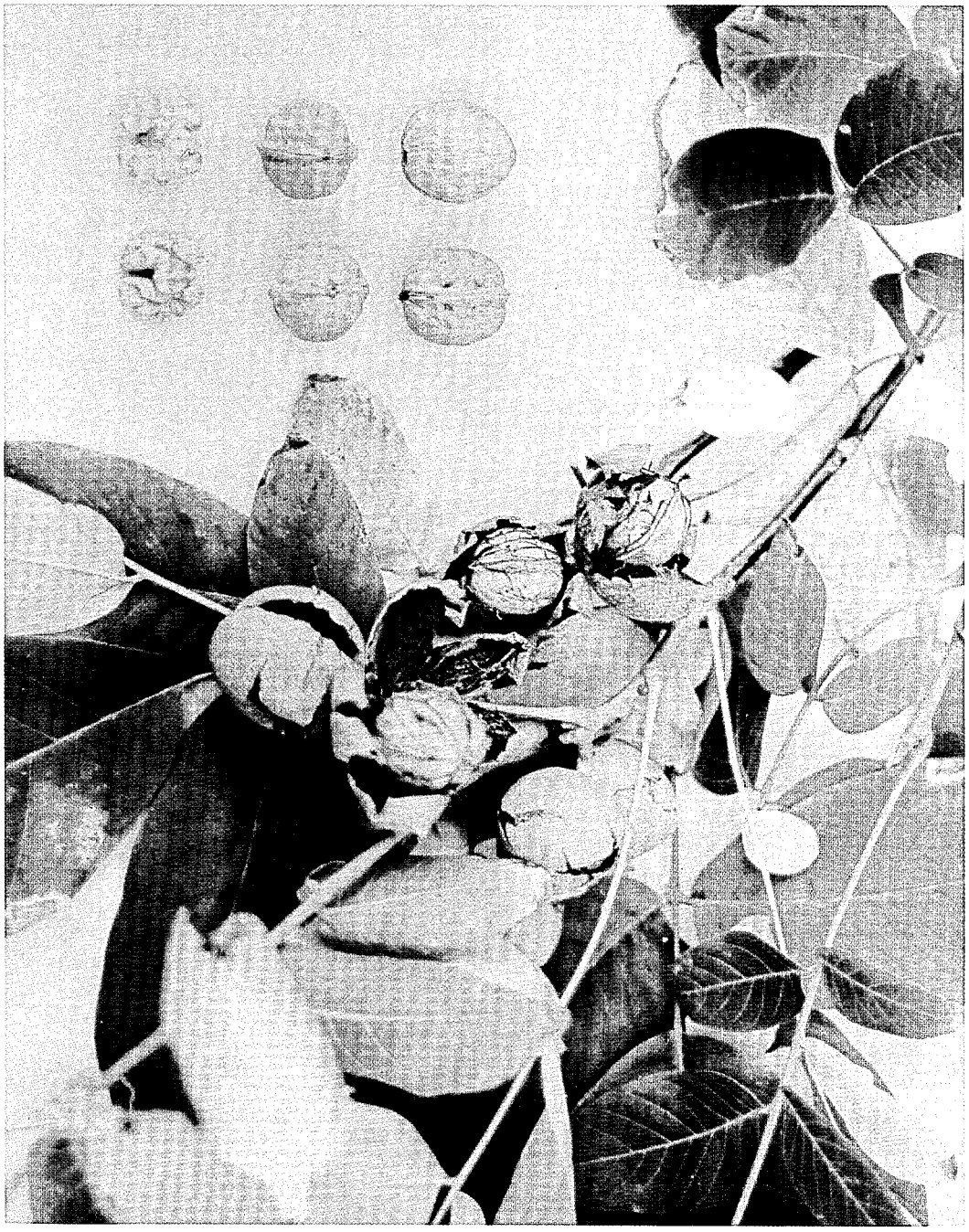

* * * * *